United States Patent
Jha et al.

(10) Patent No.: US 10,500,138 B2
(45) Date of Patent: Dec. 10, 2019

(54) POLYPHENOLS/PEG BASED HYDROGEL SYSTEM FOR A DENTAL VARNISH

(71) Applicant: DENTSPLY SIRONA Inc., York, PA (US)

(72) Inventors: Amit Jha, Dover, DE (US); Thomas C. Simonton, Mount Wolf, PA (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/939,507

(22) Filed: Mar. 29, 2018

(65) Prior Publication Data

US 2018/0296444 A1    Oct. 18, 2018

Related U.S. Application Data

(60) Provisional application No. 62/478,195, filed on Mar. 29, 2017.

(51) Int. Cl.
| | |
|---|---|
| *A61K 6/00* | (2006.01) |
| *A61K 6/027* | (2006.01) |
| *A61K 6/04* | (2006.01) |
| *A61K 6/087* | (2006.01) |
| *A61K 8/04* | (2006.01) |
| *A61K 8/21* | (2006.01) |
| *A61Q 11/00* | (2006.01) |

(52) U.S. Cl.
CPC ............ *A61K 6/0017* (2013.01); *A61K 6/027* (2013.01); *A61K 6/04* (2013.01); *A61K 6/087* (2013.01); *A61K 8/042* (2013.01); *A61K 8/21* (2013.01); *A61Q 11/00* (2013.01)

(58) Field of Classification Search
None
See application file for complete search history.

(56) References Cited

U.S. PATENT DOCUMENTS

2011/0104081 A1* 5/2011 Scott ..................... A61K 8/86
424/53

* cited by examiner

*Primary Examiner* — Brian Gulledge
(74) *Attorney, Agent, or Firm* — Dentsply Sirona Inc.

(57) ABSTRACT

Described herein are dental treatment compositions, more particularly, a dental varnish composition useful in effective fluoridation, enhancement of remineralization the tooth enamel, and hypersensitivity through occlusion of dentine tubule. The dental varnish composition includes a hydrogel system and at least one fluoride source, wherein the dental varnish is water soluble. The hydrogel system includes at least one polyphenol having at least one phenol group, at least one polymer, and a metal ion. Described herein are also methods of making such dental varnish composition.

32 Claims, 9 Drawing Sheets

Adhesion on wet tooth
Dry tooth applied
After 2hr incubation at 37 °C
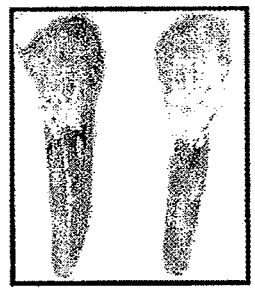
After 15hr incubation at 37 °C
FIG. 3

FIGURE 6: Synthesis of TA/GA/PEG system

| Version | Reagents reacted in 100 mL water | | | | |
|---|---|---|---|---|---|
| | Tannic Acid (gm) | PEG (gm) | Boric Acid (gm) | AlCl$_3$ (gm) | Gallic Acid (gm) |
| V1 | 5 | 5 (Mixture of 1000+4000 mol wt of PEG) | 0.25 | | |
| V2 | 4 | 5 (Mixture of 1000+4000 mol wt of PEG) | 0.25 | | 1 |
| V3 | 2.5 | 5 (8000 mol wt of PEG) | | 0.5 | 2.5 |
| V4 | 2.5 | 5 (12000 mol wt of PEG) | | 0.5 | 2.5 |
| V5 | 0.5 | 3.0 (12000 mol wt of PEG) | | 0.1 | 2.5 |
| V6 | 0.5 (from TA from Sigma) | 3.0 (12000 mol wt of PEG) | | 0.1 | 2.5 |

POLYPHENOLS/PEG BASED HYDROGEL SYSTEM FOR A DENTAL VARNISH

TECHNICAL FIELD

The present disclosure generally relates to a dental treatment composition, more particularly, a dental varnish composition useful in effective fluoridation, enhancement of remineralization the tooth enamel, and hypersensitivity through occlusion of dentine tubule. The dental varnish composition includes a hydrogel system and at least one fluoride source, wherein the dental varnish is water soluble. The hydrogel system includes at least one polyphenol having at least one phenol group, at least one polymer, and a metal ion. The disclosure also provides methods of making such a dental varnish composition.

BACKGROUND

Dental caries and hypersensitivity are two very common dental diseases. It is known that dental varnishes such as fluorides are capable to treat both dental caries and hypersensitivity. Fluorides form the protective layer of $CaF_2$ on the tooth. As a result, dissolving of the tooth enamel, which chiefly consists of hydroxyapatite, under attack by acid is slowed down by forming acid resistant fluoroapatite. Fluorides also speed up the crystallization of hydroxyapatite and prevent further demineralization.

Commonly used fluoride sources are amino fluorides, stannous fluoride, acidulated phosphate fluoride, sodium monofluorophosphate and sodium fluoride. All these have certain advantages and limitations, for example amino fluorides such as N',N'-tri-(polyoxyethylene)-N-hexadecylpropylene diamine dihydrofluoride; 9-octadecylamine hydrofluoride, hexadecylamine hydrofluoride and bis-(hydroxyethyl)-aminopropyl-Nhydroxyethyloctadecylamine dihydrofluoride, because of their cation activity, have a characteristic taste, which is difficult to mask. However, even low concentrations (0.001%-F) are highly effective. Stannous fluorides, on the other hand, are not stable in aqueous preparations, have a unpleasant metallic astringent taste, irritant to gingival and also cause the discoloration due to deposition of $Sn_3F_3PO_4$. Therefore, products for prophylaxis with stannous fluoride had disappeared completely from the market for a long time.

Sodium fluoride (NaF) is a commonly used fluoride salt in varnish systems. Sodium fluorides have a basic pH, chemically stable when stored in plastic or polythene containers. NaF dissolves well in water and quickly releases very high fluoride concentrations. Sodium fluoride delivers a highly reactive fluoride ion; therefore, formulating it with a compatible abrasive is critically important for achieving the anti-caries benefit. These materials are not irritant to the gingival, and do not cause discoloration to teeth.

Acidulated phosphate fluoride (APF) on other hand is composed of NaF to which acid is added. The concentration of fluoride is 1.23%, the acid is in form of orthophosphoric acid the pH is 3.2. It is chemically stable when stored in plastic containers, and does not cause discoloration to teeth. The success of any topical fluoridated agent depends on its capability of depositing fluoride ions in the enamel as fluoroapatite and not only calcium fluoride. Compare to NaF, APF efficiently stimulates the fluoroapatite deposition on enamel by higher fluoride ion concentration and lowering the pH. Increase in the concentration of fluoride ions lead to formation of calcium fluoride and phosphate, while the presence of acid leads to break down of the outer enamel surfaces and release of calcium and phosphate. In both reactions phosphate formed. The increase in phosphate concentration causes the shift in the equilibrium of the reaction to right side that is in the direction of formation of fluoroapatite as well as hydroxyapatite crystals.

Sodium monofluorphosphates (NaMFP), unlike other ionic fluorides, consist of covalently bound fluoridated compound; thus it cannot go into solution by dissociation. It must first be hydrolyzed by bacterial phosphatases, which are present in the saliva and plaque. Therefore, NaMFP releases markedly less fluoride at very slower rate compare to other ionically soluble fluoride salts like NaF, $SnF_2$, amino fluorides. Mechanistically, ionically bound fluoride acts through dissociation of the fluoride ion and the subsequent precipitation of calcium fluoride, the monofluorphosphates ion is probably incorporated into enamel and dentine as a complex ion.

Fluoride-containing products like toothpaste, fluoride tray, mouth rinse, tablets, are usually developed for topical applications with various concentrations and application forms. Fluoride uptake into enamel is a relatively slow process and takes a longer period of contact, thus fluoride varnishes have been developed which is typically a polymeric coating containing fluoride source that presents the fluoride in close proximity to enamel for prolonged time. Varnish method has additional advantages over the other treatment methods such as prolonged contact of fluoride agent with enamel surface, act as a slow release reservoir; the amount of fluoride permanently retained in the enamel is increased; prevent/or delay caries progression by the formation of acid resistant fluoroapatite/or flurohydroxyapatite; minimize the exposure to large quantities of fluoride, these could be applied easily; quickly without the need of professional prophylaxis; eat and drink following applications. Commonly used ingredients in fluoride varnish are sodium fluoride, rosin/and synthetic resin, various solvents, flavor additives, sweetener and pigments.

Although current varnishes have shown significant success in preventing dental caries and hypersensitivity, these systems have certain limitations. Conventional fluoride varnishes are made with tree rosins and synthetic resins that are partially dissolved by organic solvents. These rosin coatings are hydrophobic and do not release sufficient fluoride in an effective manner. Moreover, solvents such as hexane or heptanes are not very biocompatible. Other conventional fluoride varnishes contain polymers dissolved in solvent such as ethyl or butyl acetate. Ethyl and butyl acetate are harsh on oral tissue, and are barely tolerable by the patient. Additionally, many conventional fluoride varnishes leave a long lasting hard coat on the teeth that must be broken and picked from the teeth. Moreover, many conventional fluoride varnishes may have a yellow color and are not aesthetically pleasing to the patient. Existing varnishes that contain sodium fluoride contain little or no water (<5%). However, sodium fluoride is soluble in water; therefore, the fluoride is insoluble and precipitate in the hydrophobic solution creating a non-homogenous mixture resulting in formation of cluster of fluoride particles and in an irregular release of fluoride. In order to interact with tooth enamel, it is essential that the precipitated fluoride must first dissolve by aqueous saliva, which usually dissolves the fluoride available on the surface of film, and has difficulty in releasing the entrapped fluoride inside the film and that delay the release of fluoride. It is a further problem that the fluoride ions released can diffuse through the hydrophobic varnish film in the direction of the tooth surface only with difficulty, and therefore mostly migrate into the oral cavity. This means that although known products can release large amounts of fluoride, only a little fluoride reaches the enamel, thus high sodium fluoride concentrations necessary for adequate fluoridation increase the risk of fluorosis.

SUMMARY

As discussed above, there is a continuing need for a varnish system that overcomes the problems of existing varnish system.

It is an object of the present disclosure to provide a one component hydrogel system based varnish, with controlled adhesive and gelation properties. In embodiments, the final varnish composition does not include an organic solvent.

To develop the hydrogel system based varnish complex of naturally occurring polyphenols, at least one polymer and metal ion were used to make a hydrogel system which crosslinks as well as rapidly adheres to a tooth enamel surface when in contact with the tooth enamel in a salivary aqueous environment.

In a first aspect of the present disclosure disclosed is a hydrogel system for use in a dental varnish composition. The hydrogel system comprises (a) at least one polyphenol having at least one phenol group; (b) at least one polymer comprising a functional group capable of forming a hydrogen bond with said polyphenol; and (c) a metal ion.

According to one embodiment of the present disclosure, the hydrogel system is capable of forming a crosslinked film while simultaneously adhering to an enamel surface of a tooth.

In a second aspect of the present disclosure herein is a dental varnish composition comprising a hydrogel system and at least one fluoride source, wherein the hydrogel system comprises (a) at least one polyphenol having at least one phenol group; (b) at least one polymer comprising a functional group capable of forming a hydrogen bond with said polyphenol; and (c) a metal ion source. The dental varnish is water soluble.

According to one embodiment of the dental varnish composition, the at least one polyphenol is selected from the group consisting of resveratrol, tannic acid, gallic acid, isoflavones, flavonols, flavones, isoflavonone, flavanones, hydroxycinnamic acids, tocopherol, anthocyanidins, procyanidin, catechin and combinations thereof.

According to another embodiment of the dental varnish composition, the at least one polymer is selected from the group consisting of polyethylene glycol, polyethyleneimine, poly(N-isopropylacrylamide) (PNIPAM), polyacrylonitrile, polyoxazoline, poly(N-vinylpyrrolidone) (PVPON), poly(2-alkyl-2-oxazoline)s, poly(2-methyl-2-oxazoline), poly(2-ethyl-2-oxazoline), polyvinyl alcohol, pluronic, polyacrylic acid, polymethyl meth acrylic acid, poly methyl acrylic acid, Poly(vinylamine) hydrochloride, Poly(L-lysine hydrobromide), Poly(allylamine), Poly(allylamine hydrochloride), Poly(4-aminostyrene), Poly(N-methylvinylamine), Poly (ethylene glycol) bis (2-aminoethyl), Poly(diallyldimethylammonium chloride), Poly(2-vinyl-1-methylpyridinium bromide), Poly (N-ethenylformamide), Polyacrylamide (PAM), Chitosan, Poly(benzyl methacrylate), Poly(iso-butyl acrylate), Poly(n-butyl acrylate), Poly(tert-butyl acrylate), Poly(iso-butyl methacrylate), Poly(n-decyl acrylate), Poly (ethyl acrylate), Poly(glycidyl methacrylate), Poly(2-hydroxyethyl methacrylate), Poly(2-hydroxyethyl methacrylic acid), Poly(2-hydroxypropyl methacrylate), Poly(lauryl acrylate), Poly(octadecyl methacrylate), Poly(iso-propyl methacrylate), Poly(β-amino ester), Polyester, Polycarbophil, Poly(acrylamide/acrylic acid), Poly(2-ethyl-2-oxazoline), Poly(hexamethyleneadipamide), Poly(hexamethylenesebacamide), Polymethacrylamide, Polyaniline, Poly(2-methacryloxyethyltrimethylammonium bromide), Poly (lysine), Poly(N-vinylpyrrolidone), Poly(lactic acid), Poly (acryloyl chloride), Poly(ethylene glycol) 2-mercaptoethyl ether acetic acid, and mixtures thereof.

According to another embodiment of the dental varnish composition, the metal ion source includes a divalent or trivalent metal ion source, and mixtures thereof.

According to one embodiment of the dental varnish composition, the at least one fluoride source is selected from the group consisting of aluminum fluoride, indium fluoride, stannous fluoride, titanium fluoride, amine fluoride, sodium fluoride, hydro fluorosilicate, sodium fluorosilicate, potassium fluoride, disodium monofluorophosphate, acidulated phosphate fluoride, potassium fluoride, and mixtures thereof.

According to another embodiment of the dental varnish composition, the hydrogel system promotes increased adhesion of the varnish composition to a tooth surface.

In a third aspect of the present disclosure disclosed is a method of preparing a dental varnish composition, said method comprising: (a) dissolving at least one polyphenol having at least one phenol in a solvent to form a polyphenolic solution; (b) adding an antioxidant and metal ion source to the polyphenolic solution; (c) mixing the polyphenolic solution with a polymer solution to prepare a hydrogel system; (d) removing the solvent from the hydrogel system; and (e) mixing the hydrogel system with a fluoride source to form the dental varnish.

The hydrogel system based varnish of the present disclosure has surprisingly shown much better dissolution of fluoride and higher uptake to enamel and an effective fluoridation and enhancement of remineralization of the tooth enamel. It is further expected that the present hydrogel system based varnish offers several advantages over the existing varnish, for example, soluble in aqueous buffers at physiological pH, instead of in a toxic organic solvent; the base polymer system of the varnish is naturally derived and highly biocompatible/and bioactive, instead of being based on a synthetic polymeric resin; the varnish adheres to/crosslinks rapidly to enamel upon contact with the enamel surface in an aqueous environment; there is no need to dry the tooth surface before applying the varnish; low viscosity allows a higher uptake of the varnish components into the enamel and cavities; requires low concentration of fluoride in the varnish.

Further, the dental varnish composition including the hydrogel system of the present disclosure may be useful in occlusion of dentine tubule.

Other aspects will be set forth in the description which follows, and in part will be apparent from the description or may be learned from the practice of the present disclosure.

BRIEF DESCRIPTION OF THE FIGURES

The above-mentioned aspects, as well as other aspects, features, and advantages of the present disclosure is described below in connection with various embodiments, with reference made to the accompanying figures.

DETAILED DESCRIPTION

Some of the terms used in the present disclosure are defined below:

As used herein, the term "dental varnish" includes a composition topically applied to the tooth surface for fluoride therapy. Typically, a dental varnish includes a high concentration of fluoride.

As used herein, the terms "tooth structure" and "tooth surface" mean any part of an individual's teeth to which fluoride may be absorbed or bound. As such, tooth structure and tooth surface includes, but is not limited to, tooth enamel, incipient enamel lesions, hydroxyapatite in the enamel, dentin, and cementum.

As used herein, the term "hydrogel system" means a physically or chemically crosslinked polymer network with a high water content.

As used herein, the term "remineralization" means crystallization of calcium and phosphate ions into in demineralized tooth enamel.

Disclosed herein are a hydrogel system, a dental varnish composition comprising the hydrogel system and methods of using dental varnish composition for effective fluoridation and enhancement of remineralization the tooth enamel, occlusion of dentine tubule and inhibition of dental plaques biofilm.

Hydrogel System

Figure 1:
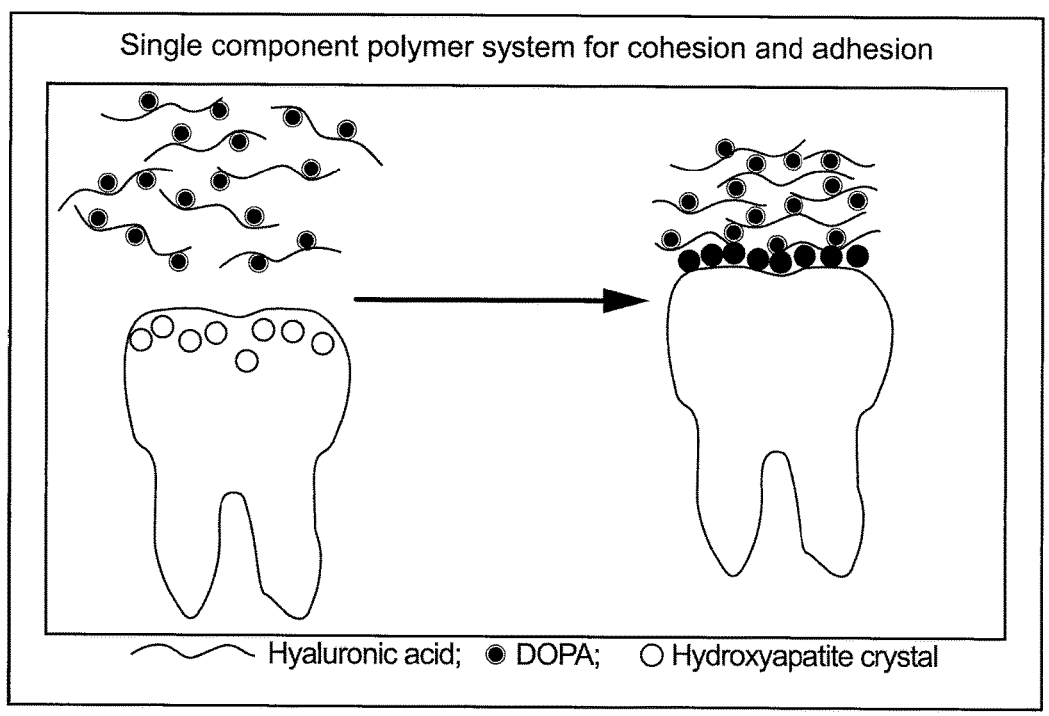
FIG. 1: Single component polymer system for cohesion and adhesion

To develop a water soluble varnish system, a water soluble polymer or hydrogel system should form a crosslinked film (that is cohesive with itself) while simultaneously adhering to an enamel surface of a tooth when the varnish comes into contact with the enamel, even under wet or damp conditions, and under physiological pH and temperature. This is all done under physiological and natural conditions found in a patient's mouth as depicted in FIG. 1.

In nature there are many natural substances that have unexpected adhesive features. One example of an adhesive found in nature is the adhesive proteins used by mussels to adhere to rocks and stones. Thus, in order to design a novel hydrogel system suitable for use in dental applications, naturally available polyphenolic molecules having at least one phenol group/polymer/metal ion complex based polymeric complex were developed.

In a first aspect of the present disclosure there is provided a hydrogel system for use in a dental varnish, the hydrogel system comprises (a) at least one polyphenol having at least one phenol group; (b) at least one polymer comprising a functional group capable of forming a hydrogen bond with said polyphenol; and (c) a metal ion.

In certain embodiments of the hydrogel system disclosed herein, the at least one polyphenol is selected from the group consisting of resveratrol, tannic acid, gallic acid, isoflavones, flavonols, flavones, isoflavonone, flavanones, hydroxycinnamic acids, tocopherol, anthocyanidins, procyanidin, catechin and combinations thereof.

In certain embodiments of the hydrogel system disclosed herein, the at least one polyphenol includes a phenol group selected from the group consisting of catechol, pyrogallol and combinations thereof.

In certain embodiments of the hydrogel system disclosed herein, the at least one polyphenol having at least one phenol group includes tannic acid (TA) and/or gallic acid (GA).

Similar to mussel adhesive proteins, tannic acid and gallic acid are naturally available polyphenolic molecules. The presence of di and tri hydroxyl functional group in tannic acid and gallic acid in the meta and para position of the benzoic acid facilitates high binding affinity to different substrates, including but not limited to electrostatic, hydrogen bonding, and hydrophobic interactions.

Figure 2:
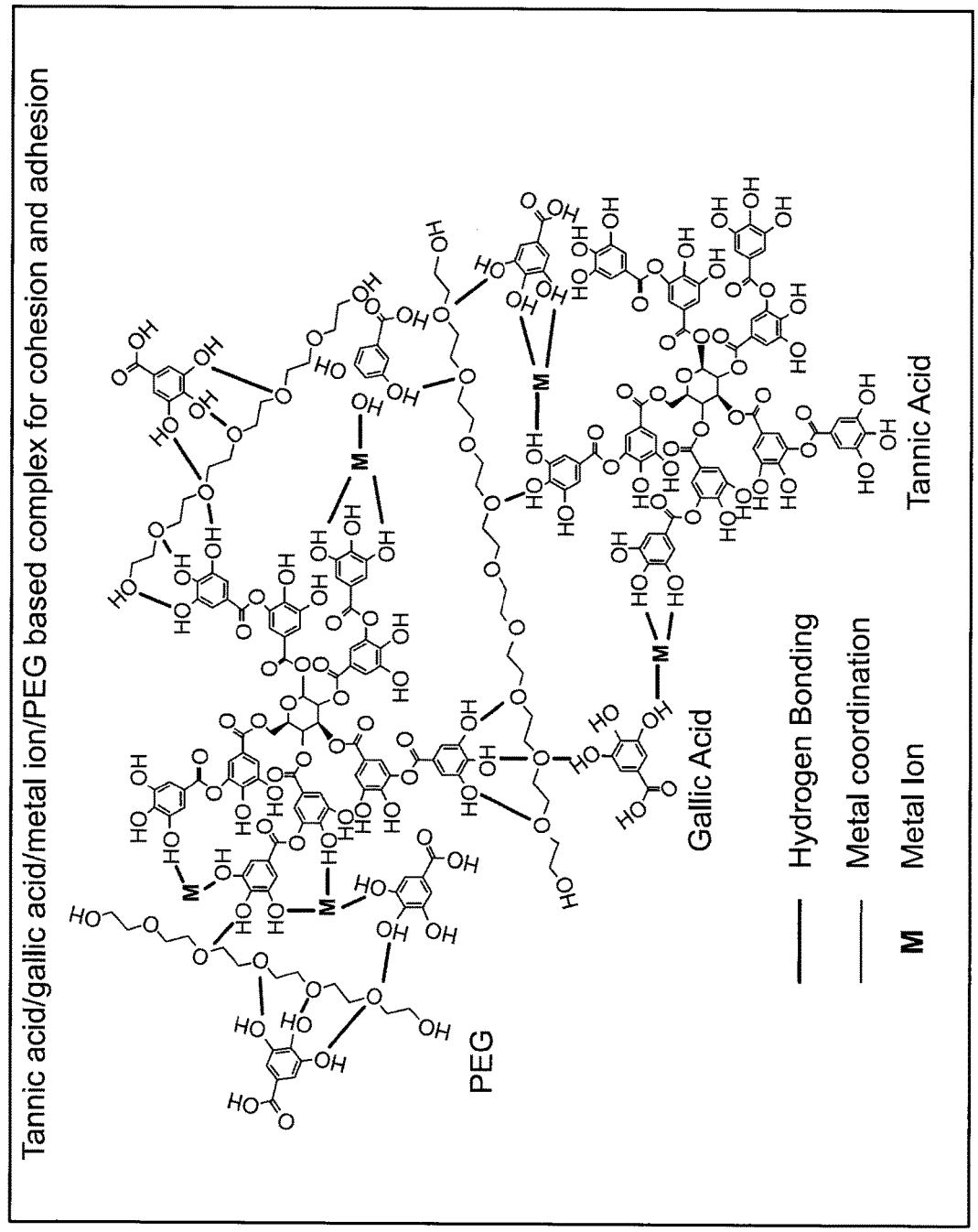
FIG. 2. Tannic acid/gallic acid/metal ion/PEG based complex for cohesion and adhesion FIG. 3. Adhesion test performed of Tannic acid/gallic acid/metal ion/PEG based hydrogel system on wet and dry bovine teeth FIG. 4. pH Titration of Tannic acid/gallic acid/metal ion/PEG based complex FIG. 5. Adhesion of varnish containing both stannous fluoride and sodium fluoride on wet bovine teeth; staining with mustard and turmeric FIG. 6. Synthesis of TA/GA/PEG system FIG. 7. Calcium absorption by Tannic acid/gallic acid/metal ion/PEG based hydrogel system FIG. 8. SEM: occlusion of dentinal tubule FIG. 9. Demonstrates the adhesive and cohesive chemistries of tannic acid

Pyrogallol groups in tannic acid and gallic acid can form a functional polymeric adhesive by two different approaches. First, forming three-dimensional networks through intermolecular hydrogen bonding with aqueous solution of a polymers. Second, pyrogallol group of tannic acid and gallic acid strongly crosslink with at least one metal ion by forming robust and reversible complexes with an aqueous solution of metal ions. In our system, both approaches of hydrogel formation are combined in one system to form hydrogel varnish, as shown in FIG. 2. Relative concentration of PEG/TA/GA/metal ions, pH, end functional groups of the PEG, number of PEG arms, are factors that regulate adhesion and cohesive properties of varnish.

The molecular basis for adhesion is the reversible coordination of metal oxides, π-π interactions with various synthetic polymers, and irreversible covalent bonding to any surface. For cohesive function, catechol undergoes pH dependent oxidative reactions by the catechol and pyrogallol/gallol-to-quinone transition. Therefore, tannic acid is a reasonable candidate for the design of a hydrogel system that can function as both an adhesive and cohesive material depending on the external environment.

In certain embodiments of the hydrogel system disclosed herein, the hydrogel system may include a polymer having a functional group capable of forming a hydrogen bond with the polyphenol.

The functional group may be hydroxy, amine, thiol, carboxyl, carbonyl, ester, imine, amide, nitrile or any suitable functional group capable of forming a hydrogen bond with the polyphenol as would be understood by person of ordinary skill in the art.

In certain embodiments of the hydrogel system disclosed herein, the at least one polymer with hydroxyl group is polyethylene gylcol or polyvinyl alcohol.

In certain embodiments of the hydrogel system disclosed herein, the at least one polymer includes an amino group, such polymer includes but is not limited to, poly(vinylamine) hydrochloride, poly(L-lysine hydrobromide), poly(allylamine), poly(allylamine hydrochloride), poly(4-aminostyrene), poly(N-methylvinylamine), poly(ethylene glycol) bis (2-aminoethyl), poly(N-vinylpyrrolidone), poly(2-alkyl-2-oxazoline)s, poly(2-methyl-2-oxazoline), poly(2-ethyl-2-oxazoline), or poly(diallyldimethylammonium chloride).

In certain embodiments of the hydrogel system disclosed herein, the at least one polymer with amido group includes but is not limited to, poly (N-ethenylformamide), polyacrylamide (PAM), or poly(hexamethyleneadipamide), poly (hexamethylenesebacamide), polymethacrylamide, poly(N-isopropylacrylamide), and nylon.

In certain embodiments of the hydrogel system disclosed herein, the at least one polymer may have an imine group, for example a polyethyleneimine.

In certain embodiments of the hydrogel system disclosed herein the at least one polymer may have a nitrile group, for example a polyacrylonitrile.

In certain embodiments of the hydrogel system disclosed herein the at least one polymer may have a thiol group, for example a poly(ethylene glycol) 2-mercaptoethyl ether acetic acid.

In certain embodiments of the hydrogel system disclosed herein the at least one polymer may have a carboxy group, for example the polymer may be, but is not limited to, a polyacrylic acid, a polymethyl meth acrylic acid, a poly methyl acrylic acid, a poly(2-hydroxyethyl methacrylic acid), a poly(lactic acid), and polycarbophil.

In certain embodiments of the hydrogel system disclosed herein the at least one polymer with an ester group includes but are not limited to poly(benzyl methacrylate), poly(isobutyl acrylate), poly(n-butyl acrylate), poly(tert-butyl acrylate), poly(iso-butyl methacrylate), poly(n-decyl acrylate), poly(ethyl acrylate), poly(glycidyl methacrylate), poly(2-hydroxyethyl methacrylate), poly(2-hydroxypropyl methacrylate), poly(lauryl acrylate), poly(octadecyl methacrylate), poly(iso-propyl methacrylate), poly(β-amino ester), and polyester.

In certain embodiments of the hydrogel system disclosed herein, the at least one polymer may be a macromolecule such as nylon, pullulan, gellan gum, hyaluronic acid, starch, cellulose, chitosan, chitin, xanthan gum, guar gum, dextran, alginate, collagen, gelatin, lignins, carbohydrates, silk, proteins, peptides, and DNA.

In further embodiments, the polymer is selected from polyethylenegylcol, polyethyleneimine, poly(N-isopropylacrylamide) (PNIPAM), polyoxazoline, poly(N-vinylpyrrolidone) (PVPON), poly(2-alkyl-2-oxazoline)s, poly(2-methyl-2-oxazoline), poly(2-ethyl-2-oxazoline), pullulan, gellan gum, hyaluronic acid and mixtures thereof.

In certain embodiments of the hydrogel system disclosed herein, the metal ion source includes a divalent, a trivalent metal ion source, or mixtures thereof.

It will be understood that there is no particular limitation to the source of the metal ions.

Examples of suitable divalent ion source include but are not limited to a salt of calcium, zinc, magnesium, tin, strontium, chromium, manganese, beryllium, barium, cobalt, nickel, lead and copper. Typically, however, salts are selected from the group consisting of calcium chloride, stannous fluoride, stannous chloride, zinc chloride etc.

Examples of suitable trivalent ion source include but are not limited to a salt of aluminum, iron, chromium, bismuth, manganese, cobalt and indium. Typically, however, salts are selected from the group consisting of aluminum chloride, aluminum sulfate, iron chloride, iron oxide, and indium fluoride etc.

In certain embodiments of the hydrogel system disclosed herein, the hydrogel system further includes an anti-oxidant.

The anti-oxidant may be selected from the group consisting of boric acid, ascorbic acid, borax, sodium tetra borate, 4,4'-Biphenyldiboronic acid, Benzene-1,4-diboronic acid, 2,5-thiophenediylbisboronic acid, sulfur dioxide, uric acid, tocopherol and mixtures thereof.

In certain embodiments of the hydrogel system disclosed herein, the hydrogel system further includes a solvent.

The solvent is selected from the group consisting of water, ethyl alcohol, isopropanol, ethyl acetate, butyl acetate, isoamyl propionate, hexane, heptane, and mixture thereof.

Also disclosed herein are a method of forming a hydrogel system.

The hydrogel system of the present disclosure may be prepared by
(a) dissolving at least one polyphenol having at least one phenol in a solvent to form a polyphenolic solution;
(b) adding a metal ion source and optionally an antioxidant to the polyphenolic solution;
(c) mixing the polyphenolic solution with a polymer solution to prepare a hydrogel system.
(d) removing the solvent from the hydrogel system.

In certain embodiments of the method of preparing a hydrogel system, the at least one polyphenol is selected from the group consisting of resveratrol, tannic acid, gallic acid, isoflavones, flavonols, flavones, isoflavonone, flavanones, hydroxycinnamic acids, tocopherol, anthocyanidins, procyanidin, catechin and combinations thereof.

In certain embodiments of the method of preparing a hydrogel system, the at least one polyphenol having at least one phenol group includes a tannic acid and gallic acid.

In certain embodiments of the method of preparing a hydrogel system, the tannic acid and gallic acid are dissolved in a solvent selected from the group consisting of water, ethyl alcohol, isopropanol, ethyl acetate, butyl acetate, isoamyl propionate, hexane, heptane, and mixture thereof. In embodiments, the solvent is ethanol.

The solvent may be present in the hydrogel system in the amounts of from about 0% to about 100%, such as from about 5% to about 50%, or from about 5% to about 10% based on total volume of the starting reaction mixture.

In certain embodiments of the method of preparing a hydrogel system, the tannic acid is present in a concentration of from 0.005 g/ml to 2.8 g/ml based on total volume of the hydrogel system, such as in the range of from 0.01 g/ml to 2 g/ml or in the range of from 0.1 g/ml to 0.5 g/ml.

In certain embodiments of the method of preparing a hydrogel system, the gallic acid is present in a concentration of from 0.005 g/ml to 0.175 g/ml based on total volume of the hydrogel system, such as in the range of from 0.01 g/ml to 0.1 g/ml or in the range of from 0.02 g/ml to 0.0 g/ml.

In certain embodiments of the method of preparing a hydrogel system, the metal ion source includes a divalent, trivalent metal ion source, or mixtures thereof.

It will be understood that there is no particular limitation to the source of the metal ions.

Examples of suitable divalent ion sources include, but are not limited to, a salt of calcium, zinc, magnesium, tin, strontium, chromium, manganese, beryllium, barium, cobalt, nickel, lead and copper.

Examples of suitable trivalent ion sources, include but are not limited to, a salt of aluminum, iron, chromium, bismuth, manganese, cobalt and indium.

In certain embodiments of the method of preparing a hydrogel system, the metal ion source may be aluminum chloride.

In certain embodiments of the method of preparing a hydrogel system, the metal ion source is present in a concentration of from 0 g/ml to 1.0 g/ml based on total volume of the hydrogel system; such as in the range of from 0.01 g/ml to 0.5 g/ml or in the range of from 0.05 g/ml to 0.1 g/ml.

In certain embodiments of the method of preparing a hydrogel system, the hydrogel system further includes an anti-oxidant.

The anti-oxidant may be selected from the group consisting of boric acid, ascorbic acid, borax, sodium tetra borate, 4,4'-Biphenyldiboronic acid, Benzene-1,4-diboronic acid, 2,5-thiophenediylbisboronic acid, sulfur dioxide, uric acid, tocopherol and mixtures thereof.

In certain embodiments of the method of preparing a hydrogel system, the anti-oxidant may be added in a concentration of from 0.01 to 10 weight percent based on total volume of the hydrogel system; such as in the range of 0.05 from to 5 weight percent or in the range of from 0.1 to 1 weight percent of total varnish.

In certain embodiments of the method of preparing a hydrogel system, the polymer is selected from the group consisting of polyethylenegylcol, polyethyleneimine, poly (N-isopropylacrylamide) (PNIPAM), polyacrylonitrile, polyoxazoline, poly(N-vinylpyrrolidone) (PVPON), poly(2-alkyl-2-oxazoline)s, poly(2-methyl-2-oxazoline), poly(2-ethyl-2-oxazoline), polyvinyl alcohol, pluronic, polyacrylic acid, polymethyl meth acrylic acid, poly methyl acrylic acid, Poly(vinylamine) hydrochloride, Poly(L-lysine hydrobromide), Poly(allylamine), Poly(allylamine hydrochloride), Poly(4-aminostyrene), Poly(N-methylvinylamine), Poly (ethylene glycol) bis (2-aminoethyl), Poly(diallyldimethyl-ammonium chloride), Poly(2-vinyl-1-methylpyridinium bromide), Poly (N-ethenylformamide), Polyacrylamide (PAM), Chitosan, Poly(benzyl methacrylate), Poly(iso-butyl acrylate), Poly(n-butyl acrylate), Poly(tert-butyl acrylate), Poly(iso-butyl methacrylate), Poly(n-decyl acrylate), Poly (ethyl acrylate), Poly(glycidyl methacrylate), Poly(2-hydroxyethyl methacrylate), Poly(2-hydroxyethyl methacrylic acid), Poly(2-hydroxypropyl methacrylate), Poly(lauryl acrylate), Poly(octadecyl methacrylate), Poly(iso-propyl methacrylate), Poly($\beta$-amino ester), Polyester, Polycarbophil, Poly(acrylamide/acrylic acid), Poly(2-ethyl-2-oxazoline), Poly(hexamethyleneadipamide), Poly(hexamethylenesebacamide), Polymethacrylamide, Polyaniline, Poly(2-methacryloxyethyltrimethylammonium bromide), Poly (lysine), Poly(N-vinylpyrrolidone), Poly(lactic acid), Poly (acryloyl chloride), Poly(ethylene glycol) 2-mercaptoethyl ether acetic acid, and mixtures thereof.

In further embodiments, the polymer is selected from polyethylenegylcol, polyethyleneimine, poly(N-isopropylacrylamide) (PNIPAM), polyoxazoline, poly(N-vinylpyrrolidone) (PVPON), poly(2-alkyl-2-oxazoline)s, poly(2-methyl-2-oxazoline), poly(2-ethyl-2-oxazoline), pullulan, gellan gum, hyaluronic acid and mixtures thereof In certain embodiments of method of preparing a hydrogel system, the polymer is present in a concentration range of from 0.01 g/ml to 1.0 g/ml based on total volume of the hydrogel system, such as in the range of from 0.01 g/ml to 0.5 g/ml or in the range of from 0.1 g/ml to 0.5 g/ml.

In certain embodiments of method of preparing a hydrogel system, the resulting hydrogel system was centrifuged to remove the solvent from the hydrogel system.

Dental Varnish Compositions

In another aspect of the present disclosure there is provided a dental varnish composition comprising a hydrogel system and at least one fluoride source. The dental varnish is water soluble. The dental varnish disclosed herein does not include an organic solvent.

As discussed above the hydrogel system includes at least one polyphenol having at least one phenol group; at least one polymer comprising a functional group capable of forming a hydrogen bond with said polyphenol, at least one polymer, and a metal ion source.

In certain embodiments of the dental varnish composition disclosed herein, the the hydrogel system is present in a concentration of from about 5 weight percent to about 95 weight percent based on a total weight of the composition; such as in the range of from about 7 weight percent to 75 weight percent or in the range of from about 10 weight percent to about 50 weight percent.

In certain embodiments of the dental varnish composition disclosed herein, the fluoride source includes but are not limited to aluminum fluoride, indium fluoride, stannous fluoride, titanium fluoride, amine fluoride, sodium fluoride, hydro fluorosilicate, sodium fluorosilicate, potassium fluoride, disodium monofluorophosphate, acidulated phosphate fluoride, potassium fluoride, bismuth fluoride, zirconium tetrafluoride, sodium mono-fluorophosphate, hexafluorosilicic acid, difluorosilane, and mixtures thereof.

In some embodiment, amine fluoride is selected from the group consisting of N',N'-tri-(polyoxyethylene)-N-hexadecylpropylene diamine dihydrofluoride; 9-octadecylamine hydrofluoride, hexadecylamine hydrofluoride and bis-(hydroxyethyl)-aminopropyl-N-hydroxyethyloctadecylamine dihydrofluoride, olaflur, amine fluoride, and dectaflur.

In certain embodiments of the dental varnish composition disclosed herein, the fluoride source includes a combination of stannous fluoride and sodium fluoride.

In certain embodiments of the dental varnish composition disclosed herein, the fluoride source is present in a concentration of from about 0.01 weight percent to about 10 weight percent based on a total weight of the composition; such as in the range of from about 1 weight percent to about 8 weight percent or in the range of from about 2 weight percent to about 7 weight percent.

In certain embodiments of the dental varnish composition disclosed herein, the the dental varnish releases fluoride ions in a concentration ranging from 1000 ppm to 30,000 ppm.

The fluoride ion source may be in an amount such that it is capable of providing a high level of fluoride ion in the composition, that is at least about 1,000 ppm, and in some instances up to as much as 30,000 ppm, e.g., from about 7,000 ppm to about 27,000 ppm, from about 15,000 ppm to about 25,000 ppm, or about 22,000 or 23,000 ppm. In order to provide such a concentration in the optimal ppm range, the exact weight percentage of the fluoride ion source in the composition may vary, depending upon the stoichiometric properties of different fluoride ion sources.

In certain embodiments of the dental varnish composition disclosed herein, the dental varnish may further include at least one of a remineralization agent, a flavor additive, a thickening agent, a sweetener, an oxidant or a combination thereof.

Examples of remineralization agents include but are not limited to bioactive glass, calcium sucrose phosphate, xylitol, nano hydroxyapatite, casein phosphopeptide-amorphous calcium phosphate (CPP-ACP), and calcium sodium phosposilicate. Amount of remineralization agents in dental varnish typically comprises at least about 0.01 weight percent and is typically no greater than 50 weight percent, such as a range of remineralization agents being from 0.02 weight percent to 10 weight percent.

Examples of a flavor additive include but are not limited to peppermint, watermelon, wintergreen, spearmint, cherry, citric acid, orange, strawberry, vanilla, coconut, bubble gum flavors and mixtures thereof. Such flavoring additives may be in the dental varnish in amounts of from about 0.01 weight percent to about 5 weight percent, such as from about 0.1 weight percent to about 4 weight percent or from about 0.7 weight percent to about 3 weight percent.

Examples of a thickening agent include but are not limited to fumed silica, carboxyvinyl polymers, carrageenans, karaya, gum arabic and tragacanth, magnesium aluminum silicate in the dental varnish in amounts of from 0.1 weight percent to 10 weight percent based on a total weight of the composition, such as from 0.5 weight percent to 8 weight percent or from about 1 weight percent to about 5 weight percent.

Examples of a sweetener include but are not limited to xylitol, sorbitol, sucralose, aspartame, sodium saccharin, and mixtures thereof. Such sweeteners may be in the dental varnish in amounts of from about 0.01 weight percent to about 2 weight percent, such as from about 0.05 weight percent to about 1.5 weight percent or from about 0.08 weight percent to about 1 weight percent.

Examples of an anti-oxidant include but are not limited to boric acid, ascorbic acid, borax, sodium tetra borate, 4,4'-Biphenyldiboronic acid, Benzene-1,4-diboronic acid, 2,5-thiophenediylbisboronic acid, sulfur dioxide, uric acid, tocopherol and mixtures thereof. When present the oxide may be present in the dental varnish in amounts of from about 0 weight percent to about 2 weight percent, such as from about 0.01 weight percent to about 1 weight percent or from about 0.08 weight percent to about 1 weight percent.

In certain embodiments of the dental varnish composition disclosed herein, the pH of the composition is in a range of from pH 1 to pH 8; such as in the range of from 2 to 6 or in the range of from 3 to 5.

Also, disclosed herein are methods of preparing a dental varnish.

The dental varnish of the present disclosure may be prepared in general by
(a) dissolving at least one polyphenol having at least one phenol in a solvent to form a polyphenolic solution;
(b) adding an antioxidant and metal ion source to the polyphenolic solution;
(c) mixing the polyphenolic solution with a polymer solution to prepare a hydrogel system;
(d) removing the solvent from the hydrogel system; and
(e) mixing the hydrogel system with a fluoride source to form the dental varnish.

In certain embodiments of method of preparing a dental varnish, the polyphenol may be present in the dental varnish in amounts of from about 0.01 mmole/ml to about 50 mmole/ml based on the total volume of the hydrogel system, such as from about 0.05 mmole/ml to about 25 mmole/ml or from about 0.10 mmole/ml to about 10 mmole/ml.

In certain embodiments of method of preparing a dental varnish, the antioxidant may be present in the dental varnish in amounts of from about 0.003 mmole/ml to about 20 mmole/ml based on the total volume of the hydrogel system, such as from about 0.015 mmole/ml to about 10 mmole/ml or from about 0.03 mmole/ml to about 3 mmole/ml.

In certain embodiments of method of preparing a dental varnish, the metal ion source may be present in the dental varnish in amounts of from about 0.005 mmole/ml to about 25 mmole/ml based on the total volume of the hydrogel system, such as from about 0.01 mmole/ml to about 5 mmole/ml or from about 0.05 mmole/ml to about 2 mmole/ml.

In certain embodiments of method of preparing a dental varnish, the polymer may be in the dental varnish in amounts of from about 0.001 mmole/ml to about 50 mmole/ml based on the total volume of the hydrogel system, such as from about 0.01 mmole/ml to about 10 mmole/ml or from about 0.010 m mole/ml to about 1.0 m mole/ml.

In certain embodiments of method of preparing a dental varnish, the fluoride source is added to the hydrogel system in amounts of from about 0.01 mmole/ml to about 5 mmole/ml based on the total volume of the hydrogel system, such as from about 0.005 mmole/ml to about 2.5 m mole/ml or from about 0.001 m mole/ml to about 1.0 m mole/ml.

Properties/Uses

The pyrogallol group on TA and GA has also strong affinity to $Ca^{2+}$ ions. This strong affinity may accelerate the HAp crystal formation in enamel and tubules by capturing salivary $Ca^{2+}$ ions. The GA/metal ion complex in the tubule resulted in the remineralization of HAp in the presence of saliva and densely packed HAp crystals with a high degree of regularity and homogeneity after immersion in artificial saliva for 7 days. Relative concentration of PEG/TA/GA/metal ions, pH, end functional groups of the PEG, number of PEG arms, are factors which regulate adhesion and cohesive properties of hydrogel varnish.

In certain embodiments of the dental varnish composition disclosed herein, the hydrogel system promoted increased adhesion of the varnish composition to a tooth surface.

In certain embodiments of the dental varnish composition disclosed herein, the hydrogel system promoted in situ remineralization of a tooth surface.

In certain embodiments of the dental varnish composition disclosed herein, the hydrogel system promoted occulsion of dentine tubule.

The combined system of TA/GA/PEG and TA/GA/metal ion complex may be a potent system which can be used to design a polymeric system of much faster reactivity with tunable cohesive and adhesive properties of the dental varnish. Additionally, the hydrogel based dental varnish described herein possesses many advantages such as lower cost, nontoxicity even after ingestion, ease of use, antioxidant, anti-mutagenic, anti-carcinogenic, and anti-bacterial properties.

The disclosure discussed herein is further illustrated by the compositions described in the following Examples, but these Examples should not be construed as limiting the scope of the present disclosure.

EXAMPLES

1. Synthesis of TA/GA/PEG/Metal Based Varnish Formulation:

First, a solution containing tannic acid and gallic acid (TA/GA solution) was prepared. Tannic acid (0-3.00 g) and gallic acid (0-7.00 g) were weighed and dissolved in about 15 ml of ethanol. After complete dissolution, about 35 mL deionized water, and (0-600 mg) aluminum chloride (metal trivalent ion) and (0-500 mg) boric acid were added to the solution. In a separate container, the polyethylene glycol (PEG) (1000 to 10000 Da MWCO) was prepared in deionized water by dissolving about 3.00 gm of PEG in about 50 mL deionized water. Then, the TA/GA solution and the PEG solution were exhaustively mixed, and the solvent was removed by centrifugation for about 5 min at about 2000 rpm to collect the hydrogel system. Final color and adhesion property depends on relative ratio of gallic acid/tannic acid/PEG/aluminum chloride, pH, end functional groups of the PEG, number of PEG arms.

Figure 6:
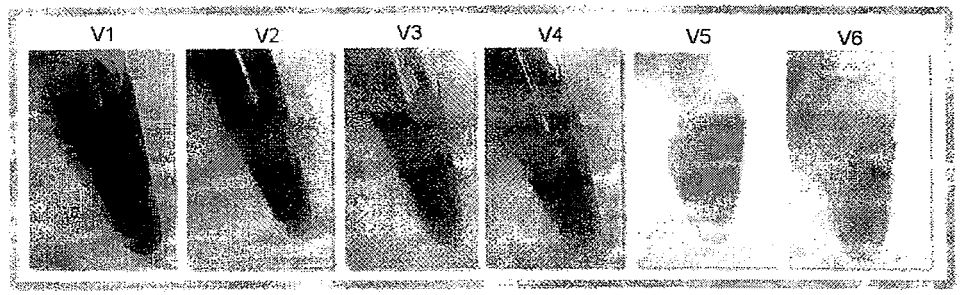

Various formulations of TA-PEG based varnish were synthesized as shown in the table and photographs of FIG. 6.

Performance Test:

After mixing $TiO_2$ during synthesis of TA-PEG, (V1) varnish formulation was used to test fluoride release and adhesion Fluoride release: Prior to fluoride release, about 5% NaF by weight was mixed with TA-PEG (v1) to result in about 22600 ppm fluoride, the fluoride release and total fluoride tests were performed.

Result: Fluoride released from TA-PEG (V1) was relatively higher (19000 ppm) compare to fluoride release (12000 ppm) from conventional varnish.

Adhesion to bovine teeth: Using the prepared formulation, adhesion test was performed on wet and dry bovine test. Then, varnish coated teeth were incubated in water for about two hours at about 37° C. Results showed a 45% adhesion on wet teeth and higher adhesion on dry teeth. Results are shown in Table 1 below:

TABLE 1

Adhesion test of Tannic acid/gallic acid/metal ion/PEG based hydrogel system on bovine teeth

| # | Varnish | Stained | Pixels | Holes | % Stained |
|---|---|---|---|---|---|
| 1 | V1 | 181850 | 398347 | 181850 | 45.7 |
| 2 | V2 | 217722 | 426623 | 271722 | 54.1 |
| 3 | V3 | 209907 | 407577 | 209907 | 51.5 |
| 4 | V4 | 167641 | 404297 | 167641 | 41.5 |
| 5 | V5 | 135250 | 397628 | 135250 | 34.0 |
| 6 | V6 | 173746 | 366437 | 173746 | 47.4 |
| ave | | | | | 45.2 |

Further testing was completed where adhesion was further improved by the addition of trivalent ($AlCl_3$) and increasing pH in the same TA-PEG (V1) formulation as shown in FIG. 3.

Figure 4:
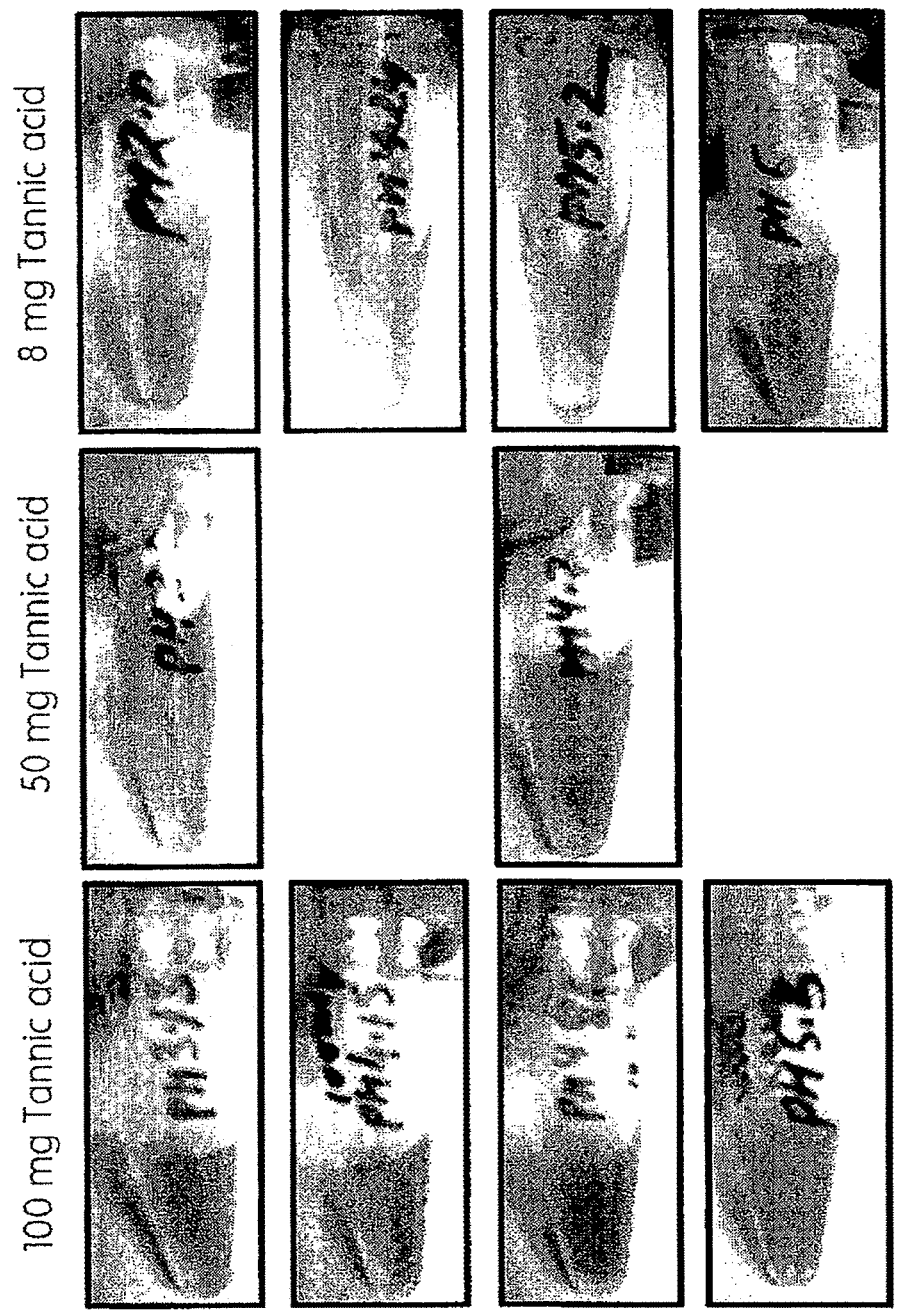

Color reduction experiment: Then, high mol wt of PEG~100 kDa was used to synthesize varnish instead of about 12 kDa of PEG because the higher molecular weight resulted in precipitation of high amount of gallic acid. Using 100 kDa PEG, Gallic acid and trivalent ions (Aluminum chloride) were reacted which resulted in white color varnish as shown in FIG. 4 (top row, left sample). However, some amount of TA is good for adhesive and viscosity of final varnish formulation. Thus, several formulations were synthesized by increasing the TA as shown in Table 2 below:

TABLE 2

REAGENTS REACTED IN 65 ML WATER

| VERSION | Gallic Acid (gm) | PEG (gm) | $AlCl_3$ (gm) | Tannic Acid (gm) |
|---|---|---|---|---|
| V7 | 3 | 0.9 (100 kDa PEG) | 0.5 | 0.0 |
| V8 | 2.95 | 0.9 (100 kDa PEG) | 0.5 | 0.05 |
| V9 | 2.90 | 0.9 (100 kDa PEG) | 0.5 | 0.10 |
| V10 | 2.975 | 0.9 (100 kDa PEG) | 0.5 | 0.025 | pH Titration: The pH of formed varnish was around 2, thus it was necessary to increase the pH without affecting the color of the final varnish formulation. Subsequently, pH titration was performed. First, the pH was increased during the synthesis, but it did not form the hydrogel complex because of limited hydrogen bonding between PEG and Gallic acid/Tannic acid. Then, the pH was sequentially increased after the synthesis of varnish of different composition as described in the table and color observed. FIG. 4 clearly demonstrates that pH can be increased up to about 5-6 without significantly affecting the color of the varnish. TA up to about 50 mg in the varnish also did not cause significant browning in the color at a pH 4-5.

Synthesis of TA/GA/PEG/Metal Based Varnish Formulation with Improved Adhesion, Fluoride Release and Fluoride Uptake:

Gallic acid (about 3 gm) was dissolved in about 15 mL ethanol and about 35 mL deionized water, and tannic acid (about 5 gm) with boric acid (about 500 mg) in about 50 mL deionized water. Separately, polyethylene glycol (12000 Da, about 1.5 gm) and polyethylene glycol (20000 Da, about 1.5 gm) were dissolved in about 50 mL deionized water, and polyethylene glycol (100000 Da, about 3 gm) was dissolved in 50 mL deionized water. Then, about 9 mL PEG (12000, and 20000 Da) was mixed with about 1 mL PEG (100000 Da) solution. Subsequently, about 30 mL GA solution was mixed with about 5-10 mL TA solution containing about 50-100 mg $AlCl_3$ and 50 mg ascorbate and pH was adjusted to about 4-4.5 and PEG solution (12000, 20000, and 100000 Da) was added. Final hydrogel system was collected by centrifugation at about 3000 rpm for about 5 min.

Using this procedure, two formulations of varnish were prepared with improved adhesion. Formulation (1) contained about 5 mL TA solution, about 50 mg $AlCl_3$ and formulation (2) contained about 10 mL TA solution and about 100 mg $AlCl_3$. Both of these formulations were tested for fluoride release and adhesion.

Adhesion:

As described in SOP PDTM-039 Rev.1, varnish was applied to wet bovine teeth and incubated in artificial saliva for about 2 hr at about 34° C. Then, teeth were stained with mustard containing turmeric powder.

TABLE 3

Percentage adhesion of varnish on bovine tooth calculated by pixel density

Percent adhesion of varnish on bovine teeth Nov. 9, 2016

| Sample | HGV 5 | Total Pixels | holes | Staind | % staind |
|---|---|---|---|---|---|
| 1 | | 377428 | 197416 | 180012 | 47.7 |
| 2 | | 299071 | 244200 | 54871 | 18.3 |
| 3 | | 337749 | 180310 | 157439 | 46.6 |
| 4 | | 577162 | 230488 | 346674 | 60.1 |
| 5 | | 572754 | 206694 | 366060 | 63.9 |
| 6 | | 702312 | 342299 | 360013 | 51.3 |
| average | | | | | 48.0 |
| | HGV 6 | | | | |
| 7 | | 229186 | 12832 | 216354 | 94.4 |
| 8 | | 967791 | 93512 | 874279 | 90.3 |
| 9 | | 877062 | 80874 | 796188 | 90.8 |
| 10 | | 849179 | 145160 | 704019 | 82.9 |
| 11 | | 768930 | 71442 | 697488 | 90.7 |
| 12 | | 862608 | 63662 | 798946 | 92.6 |
| average | | | | | 90.3 |

Figure 5:
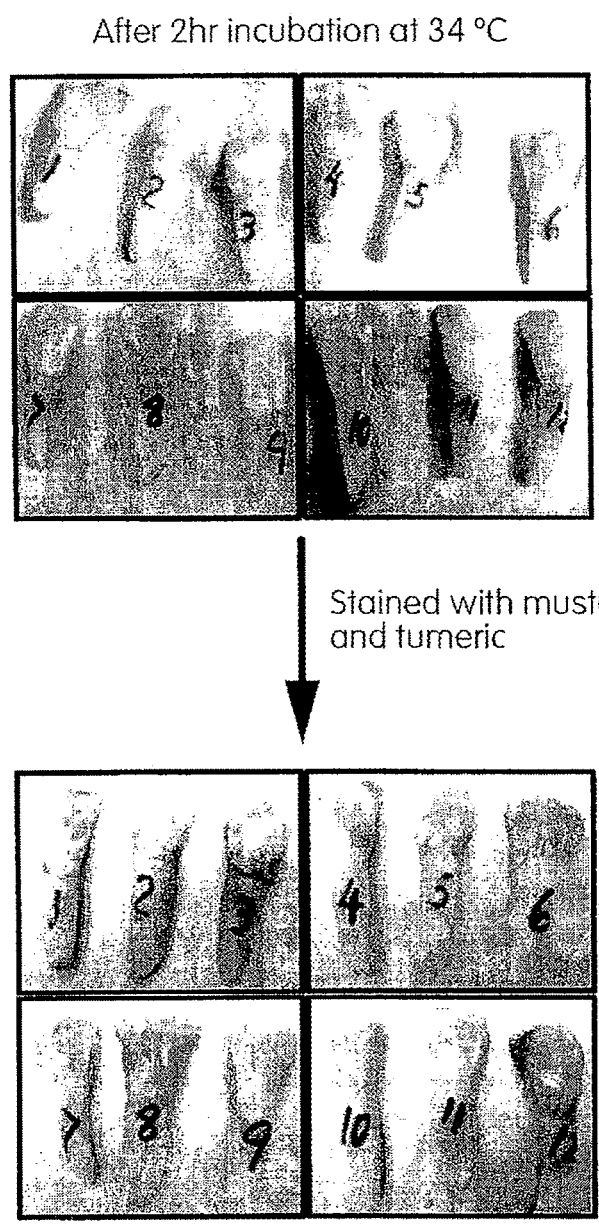

Formulation 1 with low TA supported about 48% adhesion and Formulation 2 with higher TA supported about 90% adhesion on the teeth as shown in FIG. 5 and Table 3 and confirmed by staining with turmeric containing mustard sauce.

Fluoride Release:

Next, fluoride release and total fluoride test were performed on both varnish formulations as shown in Table 4 below.

TABLE 4

Fluoride release from varnish

Fluoride release in water (ppm)

| Sample | | | | Average |
|---|---|---|---|---|
| HGV-3 | | | | |
| 1 | 0.0375 | 0.814 | 21707 | |
| 2 | 0.0251 | 0.632 | 25179 | 23174 |
| 3 | 0.0258 | 0.584 | 22636 | |
| HGV-4 | | | | |
| 1 | 0.0429 | 0.91 | 21212 | |
| 2 | 0.0279 | 0.608 | 21792 | 22226 |
| 3 | 0.0226 | 0.535 | 23673 | |

Total fluoride test in varnish (ppm)

| Sample | Read | F-ppm | NaF % | Average |
|---|---|---|---|---|
| HGV-3 Wt. g | | | | |
| 1 | 0.0317 | 0.0675 | 21293 | 4.7 | 5.5 |
| 2 | 0.0185 | 0.0501 | 27081 | 6.0 | |
| 3 | 0.0315 | 0.0826 | 26222 | 5.8 | |
| HGV-4 | | | | |
| 1 | 0.0241 | 0.0592 | 24564 | 5.4 | 5.2 |
| 2 | 0.0204 | 0.0505 | 24755 | 5.5 | |
| 3 | 0.0295 | 0.0628 | 21288 | 4.7 | |

As expected in the two tests, fluoride release was almost double than the release from conventional varnish.

Fluoride Uptake by Enamel:

For fluoride uptake experiment, sound bovine incisor enamel was embedded in the end of a plexiglass rod (¼" diameter×2" long) using methylmethacrylate. Subsequently, an artificial incipient lesion was formed in them by immersion into an about 0.1M lactic acid/0.2% Carbopol 907 50% saturated with calcium phosphate solution at about pH 5.0 for about 24 hours at about room temperature.

All (sound and lesion) specimens were preheated to about 37° C. Then, the varnishes were applied so a thin layer covered the specimens. After about one minute at about 37° C., all of the specimens were air dried and weighed once again to determine how much varnish had been used on each. None of the test varnish was forcibly removed. An attempt was made to balance the varnish amounts (±10%) based on these weights. More varnish could be added to the ones that were lower in weight but varnish was not removed from those that were heavier. To mimic the effect on an intra-oral lesioned area that might be in close proximity to a varnished area, one lesioned specimen (in a rod) was attached side by side to a rod with a varnish covered sound specimen. To simulate natural removal of the varnish in the oral cavity, each pair of specimens was then immersed into artificial saliva with mucin (about 10 ml) for about 5 minutes with constant mild agitation (about 130 rpm). After about 5 minutes, the specimens were placed into fresh artificial saliva. To mimic the release and subsequent swallowing of the fluoride from the varnishes, the first about four hours of immersion, artificial saliva was changed frequently. Then, again at about 15 and about 30 minutes and about 1 and about 4 hours, they were put into fresh artificial saliva with mucin. After the about 4 hour fresh saliva change, they stayed in the artificial saliva for about another 20 hours. They were in the artificial saliva for a total of about 24 hours. After the about 24 hours (total) at about room temperature with constant mild agitation (about 130 rpm), any visible varnish was brushed or chipped off the surface of the sound specimens. No KOH immersion was done. All the specimens (sound and lesioned) were rinsed well with deionized water. One layer of enamel was then removed from each specimen (sound and lesioned) by immersion (separately) in about 0.5 ml of about 1.0 N $HClO_4$ for about 15-seconds. A sample of each etch solution was then buffered with TISAB to a pH of about 5.2 (0.25 ml sample, 0.5 ml TISAB and 0.25 ml 1N NaOH) and the fluoride content determined by comparison to a similarly prepared standard curve (1 ml std and 1 ml TISAB).

Result: In 24 hr, tannic acid/gallic acid/PEG based hydrogel varnish promoted 1000 ppm fluoride uptake into lesioned enamel and 5500 ppm fluoride uptake into sound enamel.

Remineralization: Calcium Absorption by Hydrogel System Formulation

Catechol/pyrogallol moieties of Tannic acid and gallic acid strongly binds to various metal ions including calcium that could accelerate remineralization of teeth by hydroxyapatite formation via co-precipitation of calcium and phosphate ions from the mouth saliva. Current varnish systems in the market do not have a feature of in situ biomimetic remineralization. Tannic acid/gallic acid/polymer/metal ions based hydrogel varnish system will not only have feature of rapid fluoride release and uptake but also promote in situ biomimetic remineralization by absorbing calcium from surrounding saliva.

Hydrogel system formulation was prepared as described below:

First solution containing tannic acid and gallic acid (TA/GA solution) was prepared. Tannic acid (4.00 gm) and gallic acid (7.0 gm) were weighed and dissolved in 40 ml ethanol, and after complete dissolution, 60 mL deionized water and 300 mg aluminum chloride (metal trivalent ion) were added in the solution. In separate container, prepare the mixture of polyethylene glycol (PEG) (4000 Da, 1.5 gm) and polyethylene glycol (PEG) (12000 Da, 1.5 gm) in 100 mL deionized water. Then, TA/GA solution and PEG solution exhaustively mixed, solvent removed by centrifugation at 3000 rpm for 5 min and precipitate was collected, and used for calcium absorption experiment.

The prepared hydrogel system formulation was applied on glass slide and hydrogel system formulation applied glass slides were incubated in 25 mM calcium chloride solution for 30 min. And, as a control, hydrogel system formulation applied glass slides were incubated in DI water for 30 min.

Figure 7:
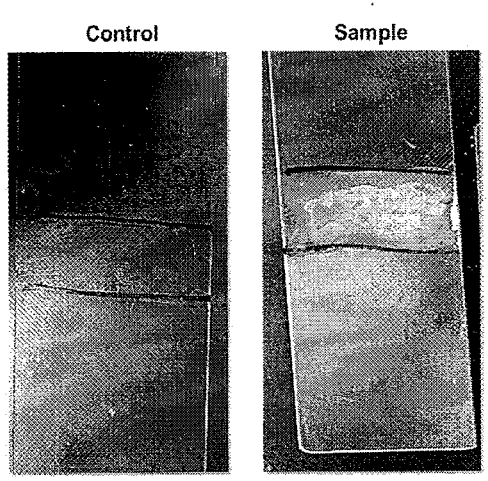

Result: In deionized water without $CaCl_2$, hydrogel system formulation applied glass slide was transparent, however hydrogel system formulation applied glass slide became whitish in color upon incubating the glass slide in deionized water containing 25 mM $CaCl_2$) which clearly indicated the absorption of $CaCl_2$ by the hydrogel system formulation dipped in $CaCl_2$) solution (FIG. 7).

2. Occlusion of Dentine Tubule

Bovine teeth were used to test occlusion of dentinal tubule using scanning electron microscopy. Samples were prepared according to the procedure using deionized water to condition the treated specimens. There test dentin substrate were prepared and stored at 5° C. in a thymol solution. Substrates were examined using an optical microscope at 200× to confirm that tubule were visible and suitable for use.

The prepared bovine teeth samples were removed from deionized water and rinsed with fresh deionized water. Excess water was blotted from the sample surface. A thin layer of varnish was applied to the test side of the tooth while the tooth was still moist. This was done with an applicator brush. Treated samples were allowed to stand for 1 minute and then half of the samples were washed for 10 seconds using tap water at moderate flow to remove varnish that was not adhered to samples. After the varnish applications, the sample was placed in artificial saliva from two hours at room temperature without any agitation of artificial saliva.

After the soak, samples were removed, rinsed gently using deionized water and allowed to air dry for a minimum of 2 hours to remove gross water. The samples were then placed in a 50° C. oven overnight to dry. The dry samples were coated with evaporated carbon and viewed under the scanning electron microscope (SEM) comparing control and treated sides.

Figure 8:
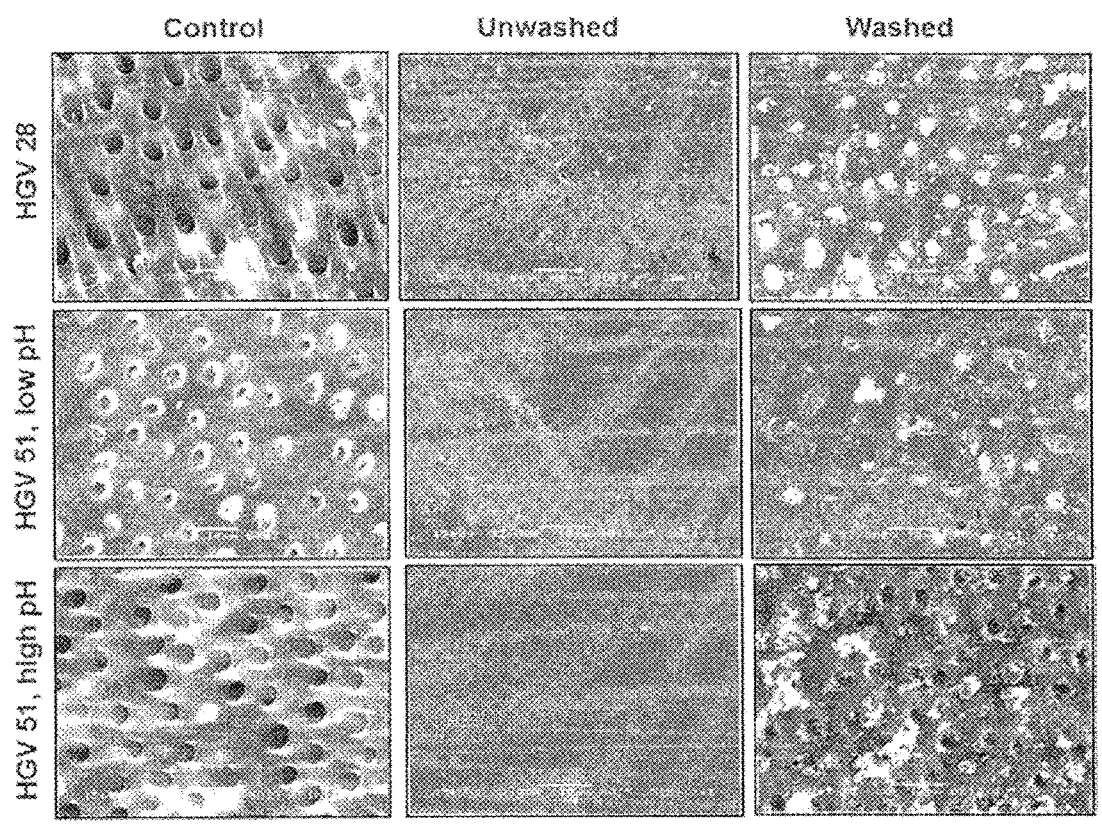
Figure 9:
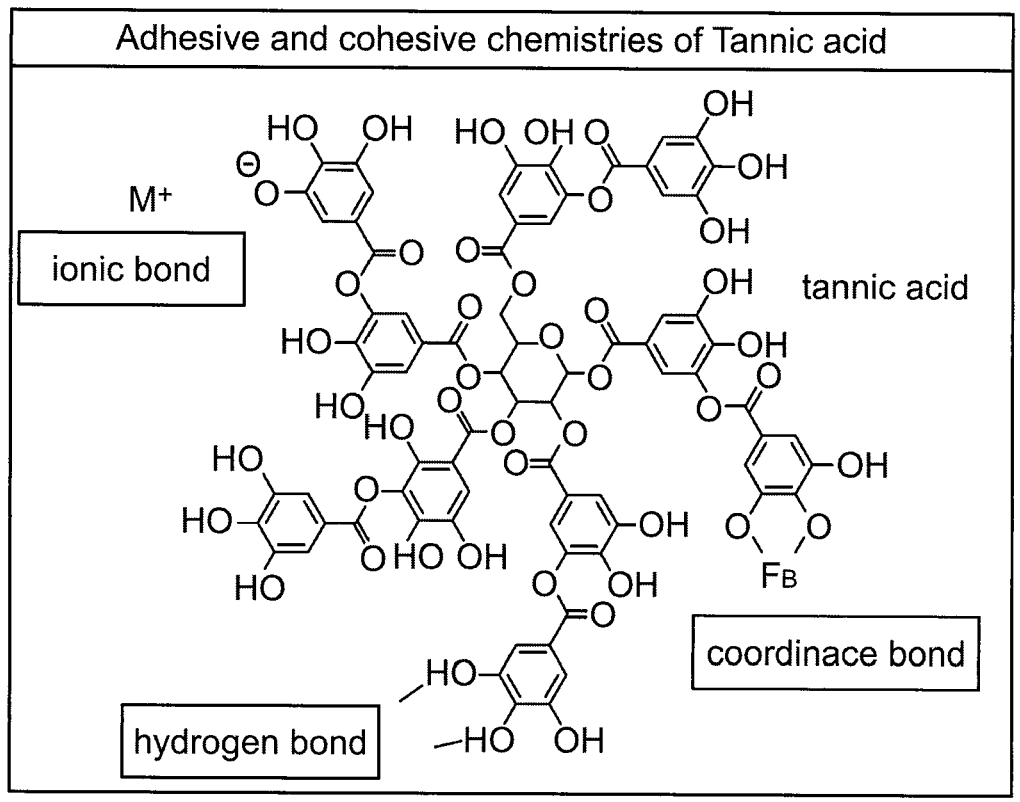

SEM micrographs (FIG. 8) showed tubule occlusion on the varnish treated sides compared to control for all samples tested. Hydrogel varnish for both group washed and unwashed have met the stated acceptance criteria and are considered effective occluding dentinal tubules under the conditions of this test.

3. Bactericidal and Biofilm Inhibition

Tannic Acid/Gallic acid being naturally occurring water soluble phenol-rich polymer contains sugar esters, mainly glucose, and phenol carboxylic acid, such as Gallic acid, hexahydroxydipenic acid. Several reports have indicated that Tannic Acid/Gallic acid has antimicrobial and bactericidal activity and also demonstrated inhibition of biofilm production and accumulation by both various Gram-positive and Gram-negative bacteria such as *Escherichia coli, Listeria monocytogenes*, oral bacteria like *Staphylococcus aureus, Streptococcus mutans*. Hertel et al (Caries Res. 2017, 51, p: 34-45) have studied the effect of tannic acid on the protective properties of in situ formed Pellicle. Tannic acid significantly improved the erosion-protective properties of the pellicle in a pH-dependent manner. Bacterial adherence and glucan formation on enamel were also significantly reduced after rinses with tannic acid as investigated by fluorescence microscopy.

In a different study, Payne et al (Infect Immun. 2013, 81, p: 496-504) have demonstrated that tannic acid inhibits *S. aureus* biofilm formation via a mechanism dependent upon the putative transglycosylase IsaA and reduced throat colonization in an animal model. Shao et al (J Food Sci. 2015, 80, M1299-305) and Kang et al (J Microbiol. 2008, 46, p: 744-50) assessed gallic acid against *Escherichia coli* (gram negative), cariogenic *Streptococcus mutans* (gram positive) and periodontopathic bacteria under different conditions, such as nutrient levels, temperatures (25 and 37° C.) and incubation times (24 and 48 h). Gallic acid significantly affected the growth curves of both test strains at 25 and 37° C. The nutrient level, temperature, and treatment time influenced the inhibition activity of GA on both growth and biofilm formation of tested pathogens.

Hydroxy groups on the catechol and pyrogallol of tannic acid/gallic acid are possibly related to their relative toxicity to microorganisms, and are able to penetrate and interact with lipid bilayers and causing the leakage of intramembranous materials and aggregation. They interact with bacterial proteins and cell wall structures, they may cause damage to cytoplasmic membranes, reduce membrane fluidity, inhibit nucleic acid synthesis, cell wall synthesis, or energy metabolism. Besides their destructive activity on bacteria, also "softer" activities leading to biofilm suppression by affecting the bacterial regulatory mechanisms such as quorum sensing or other global regulator systems are known.

It is expected that hydrogel system based varnish may demonstrate antibacterial activity and lead to inhibition of dental plaques biofilm and accumulation by various gram-positive and gram-negative bacteria.

The following example serves to provide Bactericidal and biofilm inhibition properties of Tannic acid/Gallic acid based hydrogel varnish to be verified against widely used simple model bacteria *E Coli*.

To assess the bactericidal and biofilm inhibition properties of varnish, *E coli* bacteria is cultured on varnish applied enamel like hydroxyapatite discs, then bacterial cell survival, growth rate, and biofilm formation is compared to control discs (no varnish). Then, antibacterial properties of hydrogel varnish are tested against S Mutan bacteria by determining bactericidal, growth rate and biofilm formation of oral bacteria in the presence of varnish.

Workers skilled in the art will appreciate that various modifications can be made to the illustrated embodiments and description herein without departing from the spirit and scope of the present disclosure. It is intended that all such modifications within the spirit and scope of the present disclosure be covered by the appended claims.

We claim:

1. A hydrogel system for use in a dental varnish, said hydrogel system comprising:
    (a) at least one compound having at least one phenol group;
    (b) at least one polymer comprising a functional group capable of forming a hydrogen bond with said at least one compound having at least one phenol group; and
    (c) a metal ion, wherein the at least one compound having at least one phenol group includes both tannic acid and gallic acid; and
        wherein the hydrogel system is capable of forming a crosslinked film while simultaneously adhering to an enamel surface of a tooth.

2. The hydrogel system according to claim 1, wherein the at least one compound having at least one phenol group further comprises at least one compound selected from the group consisting of resveratrol, isoflavones, flavonols, flavones, isoflavonone, flavanones, hydroxycinnamic acids, tocopherol, anthocyanidins, procyanidin, catechin and combinations thereof.

3. The hydrogel system according to claim 1, wherein the functional group is selected from the group consisting of hydroxy, amine, thiol, carboxyl, carbonyl, ester, imine, amide, and nitrile.

4. The hydrogel system according to claim 1, wherein the at least one polymer is selected from the group consisting of polyethylenegylcol, polyethyleneimine, poly(N-isopropylacrylamide) (PNIPAM), polyacrylonitrile, polyoxazoline, poly(N-vinylpyrrolidone) (PVPON), poly(2-alkyl-2-oxazoline)s, poly(2-methyl-2-oxazoline), poly(2-ethyl-2-oxazoline), polyvinyl alcohol, pluronic, polyacrylic acid, polymethyl meth acrylic acid, poly methyl acrylic acid, Poly (vinylamine) hydrochloride, Poly(L-lysine hydrobromide), Poly(allylamine), Poly(allylamine hydrochloride), Poly(4-aminostyrene), Poly(N-methylvinylamine), poly(ethylene glycol) bis (2-aminoethyl), Poly(diallyldimethylammonium chloride), Poly(2-vinyl-1-methylpyridinium bromide), Poly (N-ethenylformamide), Polyacrylamide (PAM), Chitosan, Poly(benzyl methacrylate), Poly(iso-butyl acrylate), Poly(n-butyl acrylate), Poly(tert-butyl acrylate), Poly(iso-butyl methacrylate), Poly(n-decyl acrylate), Poly(ethyl acrylate), Poly(glycidyl methacrylate), Poly(2-hydroxyethyl methacrylate), Poly(2-hydroxyethyl methacrylic acid), Poly(2-hydroxypropyl methacrylate), Poly(lauryl acrylate), Poly (octadecyl methacrylate), Poly(iso-propyl methacrylate), Poly(β-amino ester), Polyester, Polycarbophil, Poly(acrylamide/acrylic acid), Poly(2-ethyl-2-oxazoline), Poly(hexamethyleneadipamide), Poly(hexamethylenesebacamide), Polymethacrylamide, Polyaniline, Poly(2-methacryloxyethyltrimethylammonium bromide), Poly(lysine), Poly(N-vinylpyrrolidone), Poly(lactic acid), Poly(acryloyl chloride), Poly(ethylene glycol) 2-mercaptoethyl ether acetic acid, and mixtures thereof.

5. The hydrogel system according to claim 1, wherein the metal ion source includes a divalent, trivalent metal ion source, or mixtures thereof.

6. The hydrogel system, according to claim 5, wherein the divalent ion source is selected from the group consisting of a salt of calcium, zinc, magnesium, tin, strontium, chromium, manganese, beryllium, barium, cobalt, nickel, lead and copper.

7. The hydrogel system, according to claim 5, wherein the trivalent ion source is selected from the group consisting of a salt of aluminum, iron, chromium, bismuth, manganese, cobalt and indium.

8. The hydrogel system, according to claim 1, further comprising a solvent.

9. The hydrogel system according to claim 8, wherein the solvent is selected from the group consisting of water, ethyl alcohol, isopropanol, ethyl acetate, butyl acetate, isoamyl propionate, hexane, heptane, and mixtures thereof.

10. The hydrogel system, according to claim 1, further comprising an anti-oxidant.

11. The hydrogel system, according to claim 10, wherein the anti-oxidant is selected from the group consisting of boric acid, ascorbic acid, borax, sodium tetra borate, 4,4'-Biphenyldiboronic acid, Benzene-1,4-diboronic acid, 2,5-thiophenediylbisboronic acid, sulfur dioxide, uric acid, tocopherol and mixtures thereof.

12. A dental varnish composition comprising a hydrogel system and at least one fluoride source; wherein the hydrogel system comprises at least one compound having at least one phenol group; at least one polymer comprising a functional group capable of forming a hydrogen bond with said at least one compound having at least one phenol group, and a metal ion source, wherein the at least one compound having at least one phenol group includes both tannic acid and gallic acid; and, wherein the dental varnish is water soluble.

13. The dental varnish according to claim 12, wherein the at least one compound having at least one phenol group further comprises at least one compound selected from the group consisting of resveratrol, isoflavones, flavonols, flavones, isoflavonone, flavanones, hydroxycinnamic acids, tocopherol, anthocyanidins, procyanidin, catechin and combinations thereof.

14. The dental varnish according to claim 12, wherein the at least one polymer is selected from the group consisting of polyethylenegylcol, polyethyleneimine, poly(N-isopropylacrylamide) (PNIPAM), polyacrylonitrile, polyoxazoline, poly(N-vinylpyrrolidone) (PVPON), poly(2-alkyl-2-oxazoline)s, poly(2-methyl-2-oxazoline), poly(2-ethyl-2-oxazoline), polyvinyl alcohol, pluronic, polyacrylic acid, polymethyl meth acrylic acid, poly methyl acrylic acid, Poly(vinylamine) hydrochloride, Poly(L-lysine hydrobromide), Poly(allylamine), Poly(allylamine hydrochloride), Poly(4-aminostyrene), Poly(N-methylvinylamine), Poly(ethylene glycol) bis (2-aminoethyl), Poly(diallyldimethylammonium chloride), Poly(2-vinyl-1-methylpyridinium bromide), Poly(N-ethenylformamide), Polyacrylamide (PAM), Chitosan, Poly(benzyl methacrylate), Poly(iso-butyl acrylate), Poly(n-butyl acrylate), Poly(tert-butyl acrylate), Poly(iso-butyl methacrylate), Poly(n-decyl acrylate), Poly(ethyl acrylate), Poly(glycidyl methacrylate), Poly(2-hydroxyethyl methacrylate), Poly(2-hydroxyethyl methacrylic acid), Poly(2-hydroxypropyl methacrylate), Poly(lauryl acrylate), Poly (octadecyl methacrylate), Poly(iso-propyl methacrylate), Poly(β-amino ester), Polyester, Polycarbophil, Poly(acrylamide/acrylic acid), Poly(2-ethyl-2-oxazoline), Poly(hexamethyleneadipamide), Poly(hexamethylenesebacamide), Polymethacrylamide, Polyaniline, Poly(2-methacryloxyethyltrimethylammonium bromide), Poly(lysine), Poly(N-vinylpyrrolidone), Poly(lactic acid), Poly(acryloyl chloride), Poly(ethylene glycol) 2-mercaptoethyl ether acetic acid, and mixtures thereof.

15. The dental varnish according to claim 12, wherein the metal ion source includes a divalent, trivalent metal ion source, or mixtures thereof.

16. The dental varnish composition according to claim 12, wherein the at least one fluoride source is selected from the group consisting of aluminum fluoride, indium fluoride, stannous fluoride, titanium fluoride, amine fluoride, sodium fluoride, hydro fluorosilicate, sodium fluorosilicate, potassium fluoride, disodium monofluorophosphate, acidulated phosphate fluoride, potassium fluoride, and mixtures thereof.

17. The dental varnish composition according to claim 16, wherein the amine fluoride is selected from the group consisting of N',N'-tri- (polyoxyethylene)-N-hexadecylpropylene diamine dihydrofluoride; 9-octadecylamine hydrofluoride, hexadecylamine hydrofluoride and bis-(hydroxyethyl)-aminopropyl-N-hydroxyethyloctadecylamine dihydrofluoride.

18. The dental varnish composition according to claim 16, wherein the fluoride source includes both stannous fluoride and sodium fluoride.

19. The dental varnish composition according to claim 12, wherein the hydrogel system is present in a concentration of from 5 to 95 weight percent based on a total weight of the composition.

20. The dental varnish composition according to claim 12, wherein the fluoride source is present in a concentration of from about 0.01 to about 10 weight percent based on a total weight of the composition.

21. The dental varnish composition according to claim 12, wherein the dental varnish releases fluoride ions in a concentration ranging from 1000 ppm to 30000 ppm.

22. The dental varnish composition according to claim 12, wherein a pH of the composition is in a range of from pH 1 to pH 8.

23. The dental varnish composition according to claim 12, further comprising at least one of a remineralization agent, a flavor additive, a thickening agent, a sweetener, an oxidant or a combination thereof.

24. The dental varnish composition according to claim 12, wherein the hydrogel system is capable of promoting increased adhesion of the varnish composition to a tooth surface.

25. The dental varnish according to claim 12, wherein the hydrogel system is capable of promoting in situ remineralization of a tooth surface.

26. The dental varnish according to claim 12, wherein the hydrogel system is capable of promoting occlusion of dentine tubule.

27. A method of preparing a dental varnish comprising:
   (a) dissolving at least one compound having at least one phenol in a solvent to form a phenolic solution;
   (b) adding an antioxidant and metal ion source to the phenolic solution;

(c) mixing the phenolic solution with a polymer solution to prepare a hydrogel system;
(d) removing the solvent from the hydrogel system; and
(e) mixing the hydrogel system with a fluoride source to form the dental varnish, wherein the at least one compound having at least one phenol group includes both tannic acid and gallic acid.

28. The method according to claim 27, wherein the compound having at least one phenol is present in the dental varnish in amounts of from about 0.01 mmole/ml to about 50 mmole/ml based on the total volume of the hydrogel system.

29. The method according to claim 27, wherein the antioxidant is present in the dental varnish in amounts of from about 0.003 mmole/ml to about 20 mmole/ml based on the total volume of the hydrogel system.

30. The method according to claim 27, wherein the metal ion source is present in the dental varnish in amounts of from about 0.005 mmole/ml to about 25 mmole/ml based on the total volume of the hydrogel system.

31. The method according to claim 27, wherein the polymer is present in the dental varnish in amounts of from about 0.001 mmole/ml to about 5 mmole/ml based on the total volume of the hydrogel system.

32. The method according to claim 27, wherein the fluoride source is added to the hydrogel system in amounts of from about 0.01 mmole/ml to about 5 mmole/ml based on the total volume of the hydrogel system.

* * * * *